United States Patent
Akatsu et al.

(10) Patent No.: US 9,913,673 B2
(45) Date of Patent: Mar. 13, 2018

(54) LINEAR MEMBER FOR MEDICAL USE FOR BONE UNION

(71) Applicant: SYNTEC CORPORATION, Iwaki-shi, Fukushima (JP)

(72) Inventors: Kazumi Akatsu, Fukushima (JP); Jinji Ishikawa, Fukushima (JP); Takashi Abe, Fukushima (JP); Hiroshi Ochiai, Fukushima (JP)

(73) Assignee: SYNTEC CORPORATION, Iwaki-Shi (JP)

( * ) Notice: Subject to any disclaimer, the term of this patent is extended or adjusted under 35 U.S.C. 154(b) by 313 days.

(21) Appl. No.: 14/764,053

(22) PCT Filed: Jan. 31, 2013

(86) PCT No.: PCT/JP2013/052209
§ 371 (c)(1),
(2) Date: Jul. 28, 2015

(87) PCT Pub. No.: WO2014/118941
PCT Pub. Date: Aug. 7, 2014

(65) Prior Publication Data
US 2015/0359577 A1 Dec. 17, 2015

(51) Int. Cl.
*A61B 17/82* (2006.01)
*D07B 1/06* (2006.01)
(Continued)

(52) U.S. Cl.
CPC ............ *A61B 17/82* (2013.01); *A61B 17/842* (2013.01); *D07B 1/0693* (2013.01); *D07B 1/08* (2013.01);
(Continued)

(58) Field of Classification Search
CPC ....... A61B 17/82; A61B 17/84; A61B 17/842; D07B 1/0693; D07B 1/08; D07B 1/10
(Continued)

(56) References Cited

U.S. PATENT DOCUMENTS 3,114,987 A * 12/1963 Harris ................ D07B 1/10
52/223.14
3,691,751 A * 9/1972 Hiller ................ D07B 1/08
57/215

(Continued)

FOREIGN PATENT DOCUMENTS

JP 02-211164 8/1990
JP 7-508193 9/1995
(Continued)

OTHER PUBLICATIONS

International Search Report dated Feb. 26, 2013, Application No. PCT/JP2013/052209, English translation included, 4 pages.
European Search Report dated Aug. 1, 2016, 8 pages.

*Primary Examiner* — Eric S Gibson
(74) *Attorney, Agent, or Firm* — Rankin, Hill & Clark LLP

(57) ABSTRACT

A linear member for medical use having stretchability and flexibility while maintaining sufficient strength includes: an inner helical body including a plurality of helically wound wires, the inner helical body including a space portion inside, gap portions being provided in an axial direction between each wire; and an outer helical body provided outside of the inner helical body including a plurality of wires helically wound in such a manner as to form a layer along an axis of the helical body and a helical direction of the outer helical body is opposite to that of the inner helical body with gap portions being provided between each of the wires, the outer helical body being disposed to provide a multilayer structure.

4 Claims, 5 Drawing Sheets

(51) Int. Cl.
*A61B 17/84* (2006.01)
*D07B 1/08* (2006.01)
(52) U.S. Cl.
CPC .......... *D07B 2201/203* (2013.01); *D07B 2201/2029* (2013.01); *D07B 2401/201* (2013.01); *D07B 2401/2005* (2013.01)
(58) Field of Classification Search
USPC ............................................................ 606/74
See application file for complete search history.

(56) References Cited

U.S. PATENT DOCUMENTS

| | | | | |
|---|---|---|---|---|
| 3,707,839 | A * | 1/1973 | Glushko | D07B 1/08 29/505 |
| 4,936,647 | A | 6/1990 | Carroll | |
| 5,116,340 | A * | 5/1992 | Songer | A61B 17/8861 29/282 |
| 5,127,413 | A * | 7/1992 | Ebert | A61B 17/06 128/898 |
| 5,417,690 | A * | 5/1995 | Sennett | A61B 17/82 606/263 |
| 5,423,820 | A * | 6/1995 | Miller | A61B 17/82 24/129 W |
| 5,569,253 | A * | 10/1996 | Farris | A61B 17/8861 606/103 |
| 5,611,801 | A * | 3/1997 | Songer | A61B 17/82 606/103 |
| 5,725,582 | A * | 3/1998 | Bevan | A61B 17/7022 24/129 W |
| 5,772,663 | A * | 6/1998 | Whiteside | A61B 17/82 606/103 |
| 5,797,916 | A * | 8/1998 | McDowell | A61B 17/842 606/286 |
| 5,997,542 | A * | 12/1999 | Burke | A61B 17/82 606/246 |
| 6,066,141 | A * | 5/2000 | Dall | A61B 17/82 606/281 |
| 6,277,120 | B1 * | 8/2001 | Lawson | A61B 17/7053 606/263 |
| 6,387,099 | B1 * | 5/2002 | Lange | A61B 17/82 24/115 A |
| 6,475,220 | B1 * | 11/2002 | Whiteside | A61B 17/82 606/224 |
| 2005/0192581 | A1 * | 9/2005 | Molz | A61B 17/842 606/74 |
| 2009/0018583 | A1 * | 1/2009 | Song | A61B 17/705 606/246 |
| 2010/0274249 | A1 * | 10/2010 | Dell'Oca | A61B 17/82 606/74 |
| 2012/0297746 | A1 * | 11/2012 | Chou | D07B 1/02 57/230 |
| 2014/0260175 | A1 * | 9/2014 | Pourladian | D07B 1/0686 57/222 |
| 2015/0359577 | A1 * | 12/2015 | Akatsu | A61B 17/82 606/74 |
| 2017/0114497 | A1 * | 4/2017 | Liu | D07B 1/0686 |

FOREIGN PATENT DOCUMENTS

| | | |
|---|---|---|
| JP | 11-104146 | 4/1999 |
| JP | 2011-136143 | 7/2011 |
| JP | 2012-130465 | 7/2012 |
| WO | 94/00064 | 1/1994 |
| WO | 2008/102532 | 8/2008 |

\* cited by examiner

LINEAR MEMBER FOR MEDICAL USE FOR BONE UNION

TECHNICAL FIELD

The present invention relates to a linear member for medical use for internal fixation, which is used for fracture treatment. The present invention particularly relates to a linear member for medical use that can provide predetermined wrapping pressure to a fastened fractured bone part inward from an outer periphery using contraction forces in a length direction and expansion force in a diametrical direction accumulated in the linear member for medical use in a stretched state.

BACKGROUND ART

In ordinary fracture treatment, when the fractured bone is displaced, the displacement is reduced, and then fixed to wait for natural repair and fusion of the bone. Example methods for fixing a bone include non-surgical external fixation using a splint or a cast, surgical internal fixation, and external skeletal fixation.

When surgery is required for treatment of a fractured bone, displacement of the bone is reduced and then the bone is fixed inside the body using, e.g., cables, pins, screws, plates and rods of metal.

Meanwhile, with the aging population, the problem of increase in number of elderly people who suffer fractured bones has arisen. It is known that decrease in activity level of elderly people due to fractures causes secondary problems due to the fractures such as muscle weakness and dementia or the like. Therefore, it is desirable to bring such elderly people back to their ordinary life as soon as possible.

However, since elderly people have brittle bones, when a bone of an elder person is fixed using a fastening tool such as a cable, the bone may be damaged if the fastening force is excessively strong. Also, if the fastening force is weak, fixation of a fractured part is insufficient, which may adversely affects the healing process.

Therefore, there is a demand for a wire having strength enough to provide sufficient fixation when a fractured bone part is fixed, as well as stretchability enough to absorb the excess of the fastening force where a fastening force is excessively strong, along with flexibility.

In order to solve the aforementioned problems, the present inventors have already developed linear members for medical use such as those disclosed in Patent Literatures 1 and 2.

The linear members for medical use in Patent Literatures 1 and 2 have a smooth outer shape compared to existing products. Therefore, the linear members can prevent a bone to be fixed and/or surrounding tissues from being damaged and thus are applicable to children's bones having low strength and elderly people's bones having insufficient bone mass and quality.

However, although the linear members for medical use in Patent Literatures 1 and 2 are excellent linear members for medical use in terms of stretchability and flexibility, the linear members may be insufficient in strength when it is necessary to fix a thick bone such as a thighbone or a hipbone with a strong fastening force.

CITATION LIST

Patent Literature

Patent Literature 1: Japanese Patent Laid-Open No. 2011-136143

Patent Literature 2: Japanese Patent Laid-Open No. 2012-130465

SUMMARY OF INVENTION

Technical Problem

The present invention provides a linear member for medical use having higher strength while maintaining stretchability and flexibility as they are.

Solution to Problem

A linear member for medical use according to the present invention includes: an inner helical body including a plurality of helically wound wires, the inner helical body including a space portion inside, and gap portions being provided in an axial direction between the respective wires; and an outer helical body provided outside of the inner helical body, the outer helical body including a plurality of wires helically wound in such a manner that a helical direction of the outer helical body is opposite to that of the inner helical body, gap portions being provided between the respective wires, the outer helical body being disposed so as to provide a multilayer structure.

The present invention uses resilience that is a restoring force of a linear member for medical use stretched in a long-axis direction and contracted in a diametrical direction as a fastening force. In other words, a contraction force accumulated in a length direction of a linear member for medical use and an expansion force in a diametrical direction are used as wrapping pressure for fixing a fractured bone part.

In the present invention, gap portions are provided between the respective wires, thereby preventing friction between the wires. Therefore, a force applied to the linear member for medical use is not reduced by a frictional force between the wires. Accordingly, resilience of a stretched linear member for medical use is not reduced by a frictional force but is provided as a force of fastening a bone.

Also, the provision of a double-layer structure enables provision of sufficient strength and prevents rupture even in a case where a strong fastening force is applied.

In the linear member for medical use according to the present invention, a diameter of the wires forming the inner helical body and a diameter of the wires forming the outer helical body are identical to each other or different from each other, and a number of the wires forming the outer helical body is larger than a number of the wires forming the inner helical body.

For wires of an inner helical body in the linear member for medical use in Patent Literature 1, wires that are thin compared to wires of an outer helical body are used. However, the wires forming the inner helical body in the linear member for medical use according to the present invention are as thick as the wires forming the outer helical body, and thus, have high strength compared to the linear member for medical use in Patent Literature 1.

In the linear member for medical use according to the present invention, a pitch in the outer helical body is longer compare to a pitch in the inner helical body.

As a result of the pitch in the outer helical body being longer compared to the pitch in the inner helical body, a tensile strength of the linear member for medical use can be enhanced.

The linear member for medical use according to the present invention, a shape-memory alloy containing titanium is used for the wires.

For a metal member for internal fixation, an alloy that contains titanium and memorizes a certain degree of spring property is desirable from the perspective of biocompatibility. Use of a shape-memory alloy processed so as to restore original length and diameter by body temperature enables fixation of a bone with a stable fastening force. As a result of memorizing the spring property, a force applied to the linear member for medical use acts as resilience.

DESCRIPTION OF EMBODIMENT

An embodiment of the present invention will be described below with reference to the drawings.

Example

Figure 1:
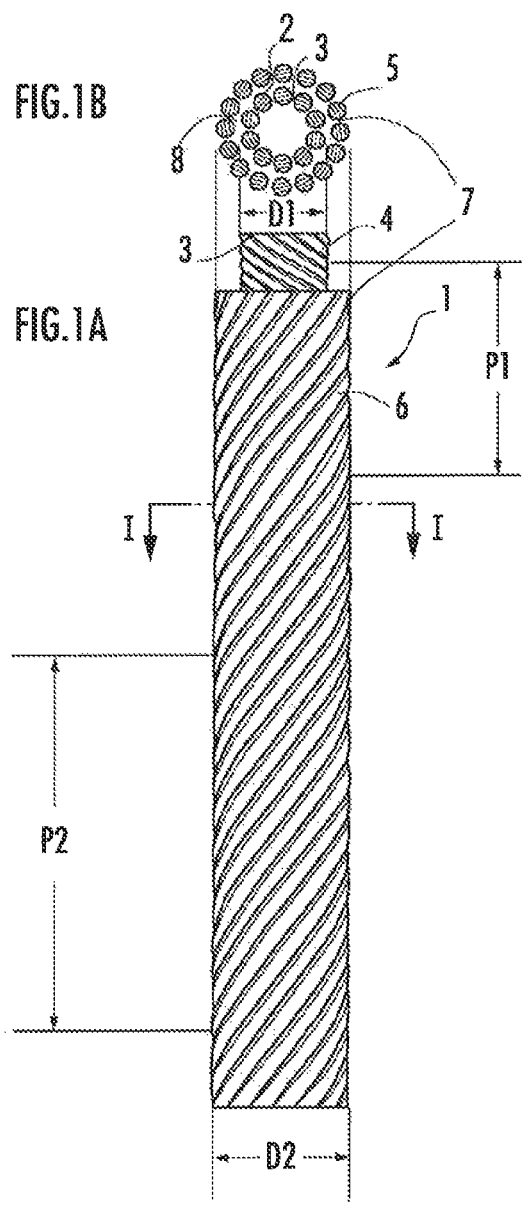
FIG. 1A and FIG. 1B are appearance diagrams illustrating a double-layer linear member for medical use according to an example.

FIG. 1A and FIG. 1B are appearance diagrams schematically illustrating a linear member for medical use according to the present invention: FIG. 1A is a front view; and FIG. 1B is an end view along line I-I indicated in FIG. 1A.

In order to form a linear member for medical use 1, a plurality of wires 2 are arranged and helically wound so as to achieve a pitch P1 and an outer diameter D1 with gap portions 3 provided between the respective wires, thereby forming an inner helical body 4. Here, the gap portions 3 between the respective wires are designed to be equal to one another.

Outside of the inner helical body 4, a plurality of wires 5 are helically wound so as to achieve a pitch P2 and an outer diameter D2 in such a manner that a helical direction of the wires 5 is opposite to that of the inner helical body 4, thereby forming an outer helical body 6. Also, a gap portion 7 is provided between each of the wires 5 forming the outer helical body 6 and the adjacent wire 5.

Since the gap portions 7 are equally provided between the respective wires in each of the helical bodies, the inner helical body 4 and the outer helical body 6, even if the linear member for medical use is in a stretched out state, the adjacent wires 5 do not come into contact with one another, causing no frictional force between the wires. Also, a gap portion 8 is provided between the inner helical body 4 and the outer helical body 6, providing a structure that avoids friction caused by contact between the helical bodies.

For the wires 2 forming the inner helical body 4 and the wires 5 forming the outer helical body 6, those having a same diameter are used, and the number of the wires 2 forming the inner helical body 4 is made smaller than the number of the wires 5 forming the outer helical body 6 to provide a design in which the outer diameter D1 of the inner helical body 4 is smaller than the outer diameter D2 of the outer helical body 6.

For the wires 2 and 5 of the inner helical body 4 and the outer helical body 6, those having a same diameter are used, which enables increase in strength compared to the linear member for medical use in Patent Literature 1 in which the wires of the inner helical body are designed to be thin.

Although the outer diameters D1 and D2 and the pitches P1 and P2 in the helical bodies can arbitrarily be designed according to, e.g., the intended use and/or the site of application of the linear member for medical use 1, it is preferable that the pitch P1 is shorter compared to the pitch P2. As described above, the pitch in the outer helical body is longer compared to the pitch in the inner helical body, it is able to increase the tensile strength of the linear member for medical use.

A member for medical use according to the example, which was manufactured for the below comparison in, e.g., strength, was fabricated actually using titanium wires having a diameter of 0.14 mm as wires, 12 wires was used for an inner helical body, 18 wires was used for an outer helical body, so as to achieve a pitch P1 of 5.2 mm (pitch in an inner helical body) and a pitch P2 of 6.9 mm (pitch in an outer helical body), and an outer diameter D1 of 0.78 mm (outer diameter of the inner helical body) and an outer diameter D2 of 1.06 mm (outer diameter of the outer helical body). The member has a structure in which a void part having a diameter of around 0.5 mm is provided at a center thereof.

Here, for a linear member for medical use according to the present invention, the diameter of wires to be used, the number of wires forming each helical body, the pitch and the outer diameter of each helical body can arbitrarily set according to a fracture site, in order to obtain necessary physical properties such as strength.

Comparative Example

Figure 2:
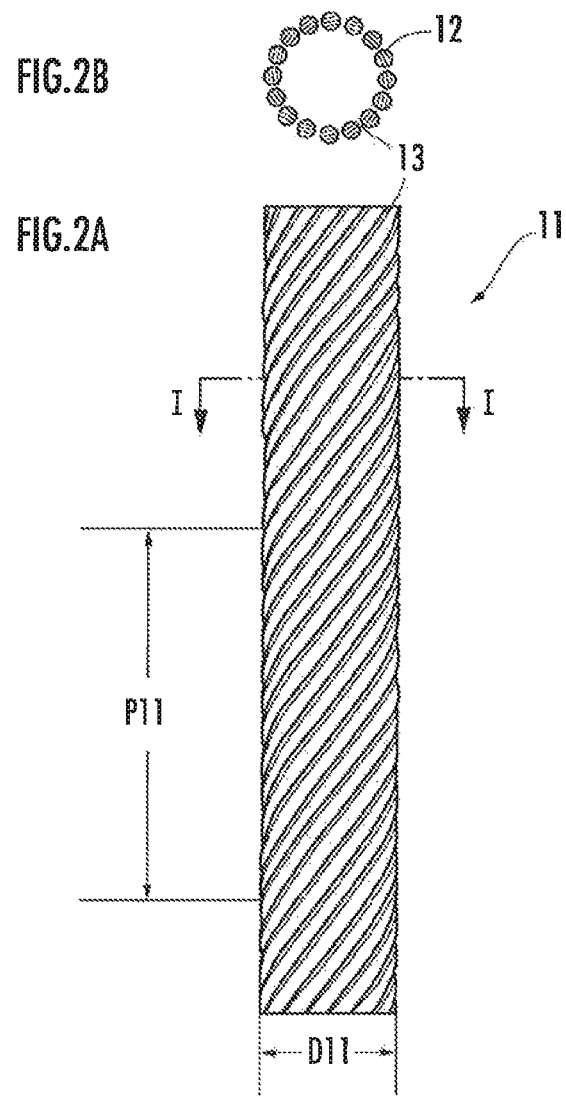
FIG. 2A and FIG. 2B are appearance diagrams illustrating a single-layer linear member for medical use according to a comparative example.

FIG. 2A and FIG. 2B are appearance diagrams schematically illustrating a linear member for medical use 11 according to a comparative example: FIG. 2A is a front view; and FIG. 2B is an end view along line I-I indicated in FIG. 2A.

In order to form the linear member for medical use 11 according to the comparative example, a plurality of wires 12 are arranged and helically wound so as to achieve a pitch P11 and an outer diameter D11 with gap portions 13 between the respective wires. Here, the gap portions 13 between the respective wires are designed to be equal to one another. The same wires as those of the example were used, and the helical body was formed so as to have the same pitch and the outer diameter as those of the example except that the helical body has a single-layer structure rather than a double layer structure.

Wires actually used in a strength test and the like were 18 titanium wires having a diameter of 0.14 mm manufactured so as to achieve a pitch P11 of 6.9 mm and an outer diameter D11 of 1.06 mm.

Physical characteristics such as stretchability and flexibility were compared and examined below for the linear member for medical use according to the example, the linear member for medical use according to the comparative example and linear members for medical use that are existing products of other companies.

Figure 3:
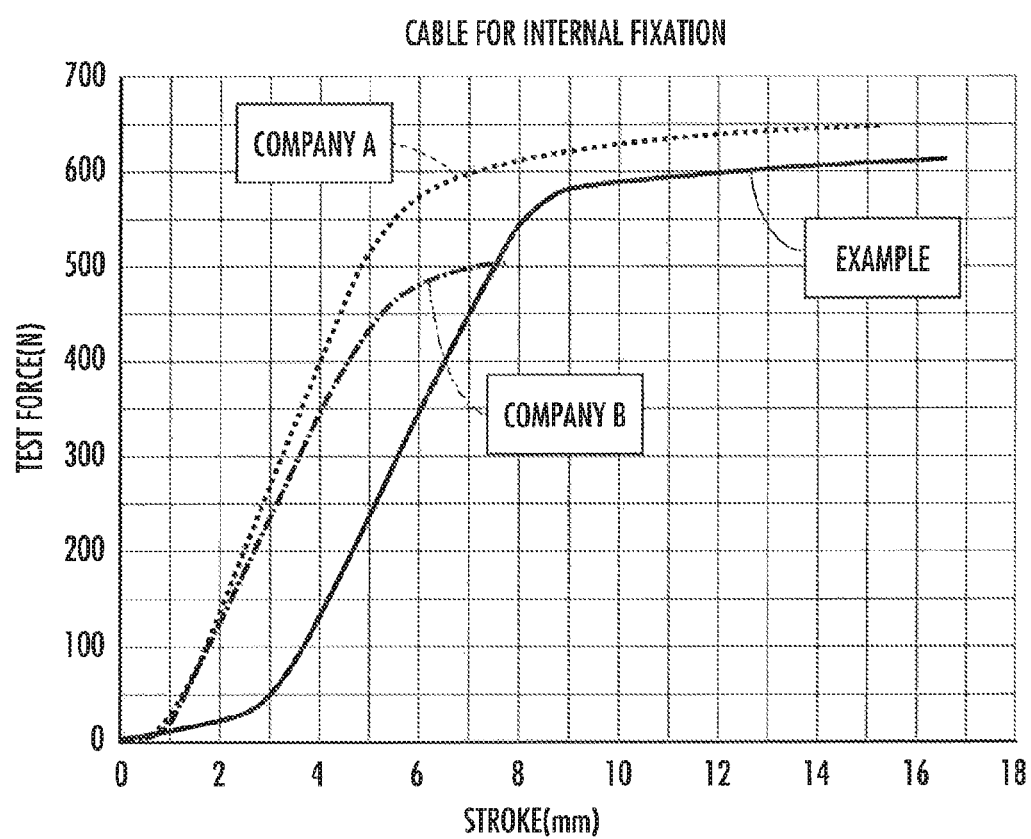
FIG. 3 is a diagram in which the example, the comparative example and products of other companies are compared in terms of flexibility.

FIG. 3 indicates measurements of respective degrees of flexibility of the linear member for medical use according to the present invention and the linear members for medical use that are products of other companies when a constant force is applied to the linear members based on JIS Z-2241.

Stretches of the linear member for medical use according to the example and the linear members for medical use that are products of other companies, company A and company B are plotted, when a test force (N) represented by the ordinary axis, was applied to the linear members for medical use each having a fixed length of 100 mm, The products of the other companies are both manufactured by twisting thin titanium wires like yarns, and do not have a void portion provided in the center like the present invention, and extend poorly and have a surface that is not smooth as that of the linear member for medical use according to the present invention.

More specifically, the company A product has a structure formed by twisting seven basic structures together, each basic structure being formed by twisting seven 0.12 mm titanium wires like a yarn, and thus is manufactured using a total of 49 wires. The company A product has a diameter of 1.05 mm, which is substantially the same as those of the linear members for medical use according to the example and the comparative example.

The company B product includes 133 wires provided by twisting 19 basic structures together, each basic structure formed by twisting seven 0.064 mm wires like a yarn. The company B product has a diameter of 0.84 mm.

As illustrated in FIG. 3, when a weak test force of not more than 50 N was applied to the member for medical use according to the present invention, the member for medical use stretched very well compared to the products of the other companies because the gap portions are provided between the wires. The linear member for medical use according to the present invention itself stretches with a weak force, and thus, flexibly moves with a weak force when fixing a bone, and is very easy to be handled by a surgeon.

Some of bones have a complicated shape, and there are various types of bone fractures. However, the linear member for medical use according to the present invention stretches with a weak force and can fasten a bone with a good fit even if the bone has an irregular shape, and can thus be used for various sites.

Also, a right end of the lines in each of the graph in FIG. 3 indicates a point where the relevant linear member for medical use ruptured because of increase in test force (N) and no further force could be applied thereto.

It is indicated the linear member for medical use of company B ruptured when a force of approximately 500 N was applied, the linear member for medical use according to the example was ruptured when a force of approximately 610 N was applied, and the linear member for medical use of company A ruptured when a force of approximately 650 N was applied.

The linear member for medical use according to the present invention is superior in strength compared to the company B product. Compared to the company A product, the linear member for medical use according to the present invention is somewhat inferior in strength, but has no problem when actually fastening a bone.

The linear member for medical use according to the example stretches at a constant rate when a test force of approximately 50 N to approximately 570 N is applied. Therefore, application of a force of approximately 50 N to approximately 570 N to a fractured bone part to fasten a fractured bone part enables the bone to be firmly fixed.

Furthermore, when a test force of no less than approximately 570 N is applied to the linear member for medical use according to the example, the force is absorbed as a stretch of the linear member for medical use. Thus, even if a strong force is applied, the bone is prevented from being damaged.

Figure 4A:
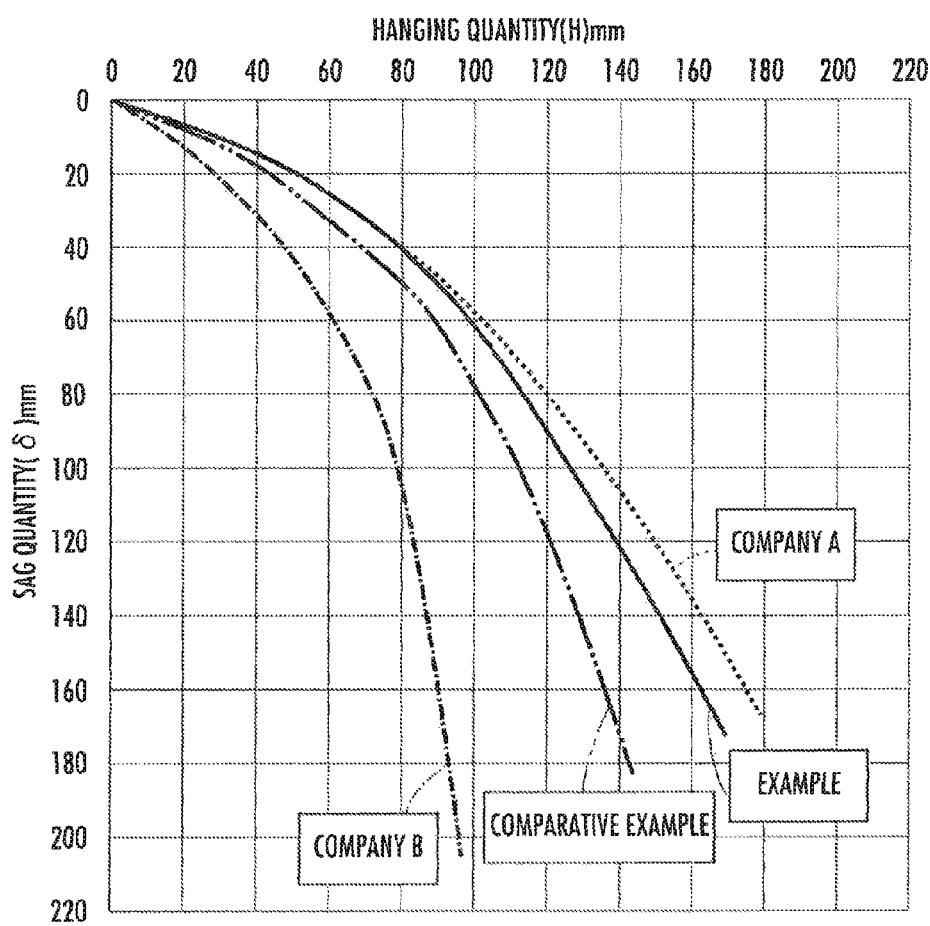
FIG. 4A and FIG. 4B are diagrams in which the example and the products of the other companies are compared in terms of stretch-force relationship.

Next, as an index representing handiness, the linear members for medical use were compared in terms of flexibility. FIG. 4A indicates comparison in flexibility among the linear member for medical use according to the present invention, the linear member for medical use according to the comparative example and the linear members for medical use that are products of the other companies.

Figure 4B:
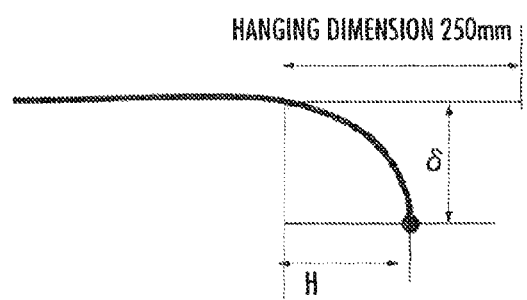

As schematically illustrated in FIG. 4B, a portion of each linear member for medical use that is 250 mm from one end thereof is a hanging end, and the other end is fixed. A relationship between a hanging quantity (H) and a sag quantity ($\delta$) when the hanging end sags under its own weight is plotted as a rough indication of flexibility.

A more flexible member sags lower under its own weight, and thus, exhibits a larger value in the sag quantity $\delta$ and a smaller value in the hanging quantity H.

As illustrated in FIG. 4, the flexibility is larger in the order of the linear members for medical use of company A, the example, the comparative example and company B.

The comparative example includes a single-layer helical body and thus is superior in flexibility compared to the member for medical use according to the example including a double-layer structure. However, the strength of the linear member for medical use according to the comparative example is insufficient for fastening a large bone such as a hipbone or a thighbone.

The linear member for medical use according to the example is not as flexible as the company B product. However, as illustrated in FIG. 3, the linear member for medical use according to the present invention stretches very well even if only a weak force is applied to fasten a bone while stretching the linear member and thus, exhibits handiness that is equivalent to or exceeds that of the B company product.

As described above, the linear member for medical use according to the present invention has excellent flexibility, and stretches well even when only a weak force is applied, and thus is very easy to handle. In addition, when a strong force is applied, the force can be absorbed by the stretch, preventing a bone from being damaged.

Figure 5:
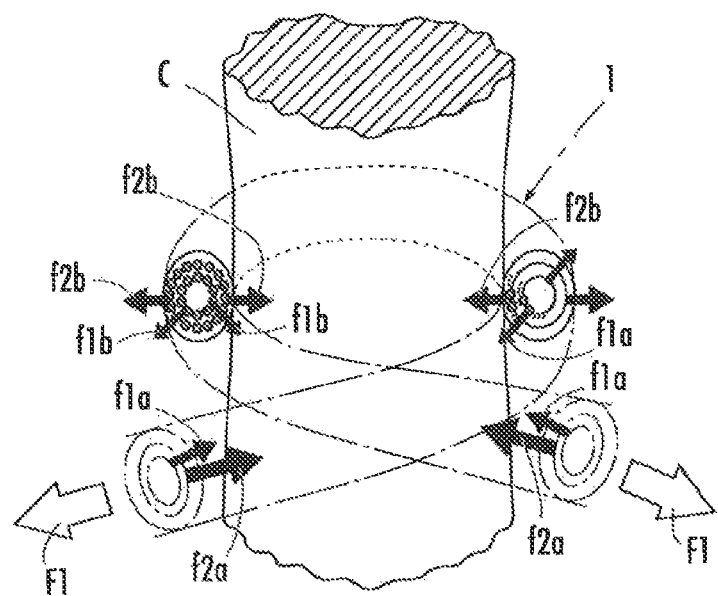
FIG. 5 is a diagram illustrating a fastened state of a fracture site fastened using the linear member for medical use according to the example.

Next, how a force acts when the linear member for medical use 1 according to the present invention is used as a surgical fastening cable, which is to be wound around a fractured bone part and fastened will be described with reference to schematic FIG. 5.

When a tensile force F1 acts on both ends of the linear member for medical use 1 (FIG. 5; the illustration of the lower end side omitted) in a length direction, an inclination angle of the helix increases, the pitch increases, the linear member for medical use 1 stretches, the gap portions are reduced, and the outer diameter of the linear member for medical use 1 (corresponding to D2) decreases.

In this case, the linear member for medical use 1 becomes a state in which a contraction force f1a of the inner helical body and a contraction force f2a of the outer helical body that urge the pitches P1 and P2 to return to the pitches P1 and P2 before the stretch, and expansion forces f1b and f2b that urges the outer diameters D1 and D2 to return to the outer diameters D1 and D2 before the stretch, are accumulated.

Cancellation of the tensile force F1 on the linear member for medical use 1 enables the linear member for medical use 1 to return to an original state the spring property.

A surgeon winds the linear member for medical use 1 around a fractured bone part, makes a tensile force F1 act thereby to stretch the linear member for medical use 1 in the length direction, and fastens the fractured bone part using the stretched linear member for medical use 1, thereby fixing the fractured bone part.

The linear member for medical use according to the present invention enables predetermined wrapping pressure to consistently act toward a center from an outer periphery of a fractured bone part the aforementioned contraction forces and the expansion forces. Furthermore, since the double-layer helical body structure is provided, it is able to obtain sufficient strength and also to fix the fractured bone part with a strong fastening force. However, as a result of providing the gap portions between the wires, the linear member for medical use stretches with a weak force and thus has flexibility.

REFERENCE SIGNS LIST

1, 11 . . . linear member for medical use
2, 5, 12 . . . wire
3, 7, 8, 13 . . . gap portion
4 . . . inner helical body
6 . . . outer helical body
D1, D2 . . . outer diameter
P1, P2 . . . pitch

The invention claimed is:

1. A linear member for medical use comprising:
an inner helical body including a plurality of helically wound first wires arranged uniformly forming a first circular cross section, the inner helical body including a space portion inside, and first gap portions being provided in an axial direction of the linear member between each of the first wires; and
an outer helical body provided outside of the inner helical body, the outer helical body including a plurality of second wires arranged uniformly forming a second circular cross section, and helically wound in such a manner that a helical direction of the outer helical body is opposite to that of the inner helical body, and second gap portions being provided in the axial direction between each of the second wires, the outer helical body being disposed so as to provide a multilayer structure,
wherein each of an inner circumference and an outer circumference of the inner helical body respectively form a same first circular shape along the axial direction, and each of an inner circumference and an outer circumference of the outer helical body respectively form a same second circular shape along the axial direction.

2. The linear member for medical use according to claim 1, wherein:
a diameter of the first wires forming the inner helical body and a diameter of the second wires forming the outer helical body are identical to each other or different from each other; and
a number of the second wires forming the outer helical body is larger than a number of the first wires forming the inner helical body.

3. The linear member for medical use according to claim 1, wherein a pitch of the outer helical body is longer than a pitch of the inner helical body.

4. The linear member for medical use according to claim 1, wherein a metal containing titanium is used for the first wires and the second wires.

* * * * *